Figure 1:
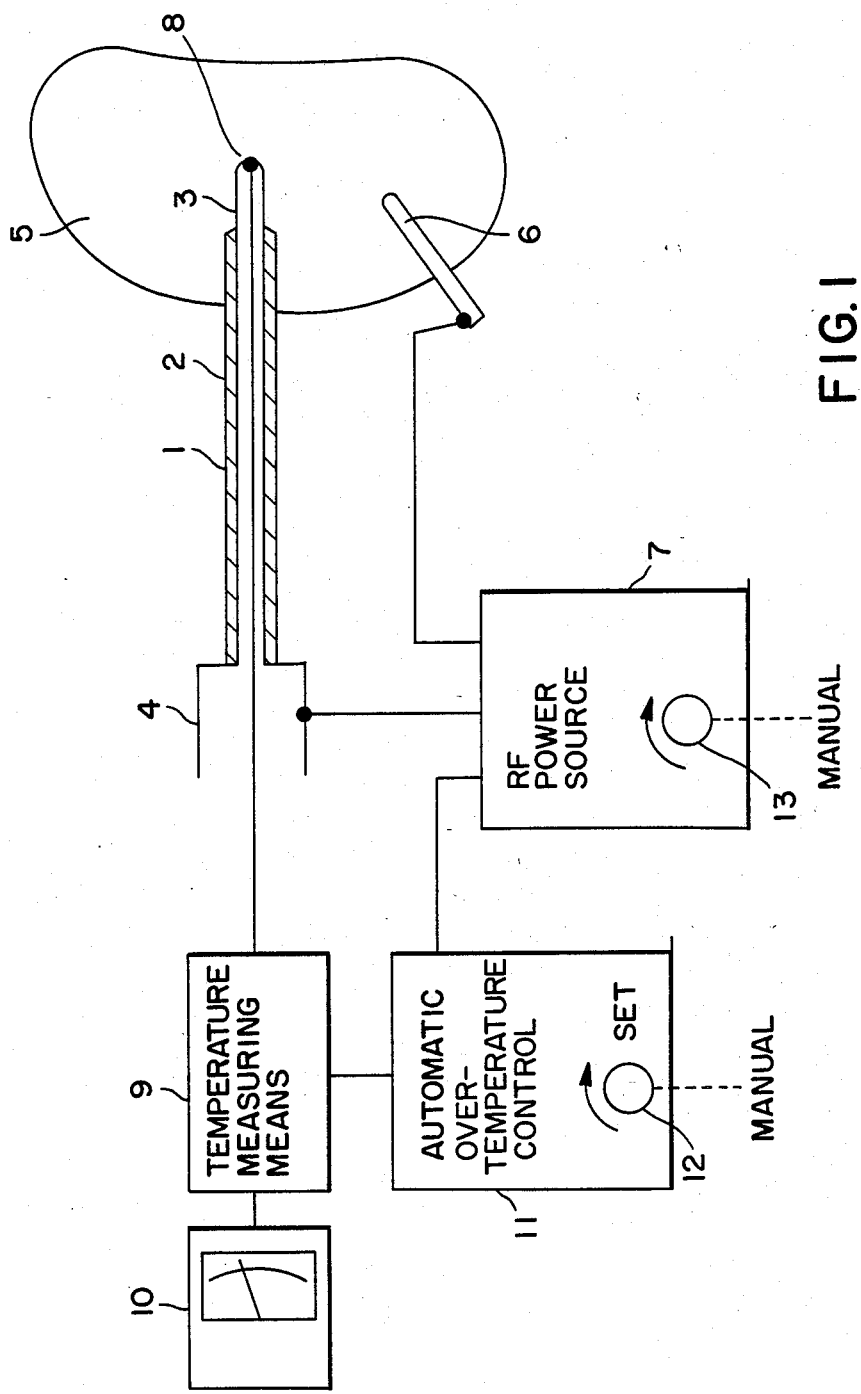

United States Patent [19]

Cosman

[11] Patent Number: 4,907,589
[45] Date of Patent: Mar. 13, 1990

[54] AUTOMATIC OVER-TEMPERATURE CONTROL APPARATUS FOR A THERAPEUTIC HEATING DEVICE

[76] Inventor: Eric R. Cosman, 872 Concord Ave., Belmont, Mass. 02178

[21] Appl. No.: 188,272

[22] Filed: Apr. 29, 1988

[51] Int. Cl.$^4$ ............................................. A61B 17/36
[52] U.S. Cl. ..................... 606/34; 128/401; 128/784; 606/41
[58] Field of Search ........... 128/303.1, 303.13–303.18, 128/395–398, 401, 804, 784

[56] References Cited

U.S. PATENT DOCUMENTS

| | | | |
|---|---|---|---|
| 4,196,734 | 4/1980 | Harris | 128/303.15 |
| 4,311,154 | 1/1982 | Sterzer et al. | 128/804 |
| 4,397,314 | 8/1983 | Vaguine | 128/401 |
| 4,411,266 | 10/1983 | Cosman | 128/303.18 |
| 4,644,955 | 2/1987 | Mioduski | 128/303.13 |
| 4,712,559 | 12/1987 | Turner | 128/804 |

Primary Examiner—Max Hindenburg
Attorney, Agent, or Firm—Richard J. Birch

[57] ABSTRACT

The use of radio frequency currents to heat and destroy neurological tissues is well known in the field of neurosurgery and typically involves monitoring of the tissue temperature as it is being heated by an in-dwelling electrode. This patent deals with an apparatus and method which enables the operator of such apparatus to be in control of the rise of temperature and the increase in radio frequency power delivered to such electrodes, and yet also to pre-set a temperature and have control circuitry and other means to prevent the electrode temperature to exceed a set temperature point. We refer to this as an over-temperature control for heat lesion generation equipment in the case of neurosurgery. The system is a hybrid between a purely manually controlled radio frequency heating unit and a completely automatically controlled radio frequency unit, the latter being such that it automatically raises the radio frequency power and feedbacks on a set temperature to stabilize the final electrode temperature. The present invention retains the important position of the human operator in establishing the rise of temperature and yet affords the advantage of temperature stabilization at a fixed end point and thereby gives the benefits of a fully automatic control system to the added asset of safety and human control.

6 Claims, 1 Drawing Sheet

AUTOMATIC OVER-TEMPERATURE CONTROL APPARATUS FOR A THERAPEUTIC HEATING DEVICE

BACKGROUND OF THE INVENTION

It is well established in neurosurgery that selected destruction of neural tissue can in many cases benefit patients with pain and other functional disorders. Typically, this invovles inserting a metal electrode with an insulated portion into the body, connecting the electrode to a source of radio frequency voltage, and heating the neural tissue at the unexposed bare tip of the electrode so as to selectively destroy a portion of nervous tissue. This is the radio frequency lesion generation technique. It was pioneered in the early fifties; see the attached review article by E. R. Cosman and B. J. Cosman, and the first papers by Dr. W. H. Sweet, Professor F. Mundinger, Wyss and Hunsperger, and Aranau, which illustrate its early development. Typically, in the most popular RF lesion generators used today (made by Radionics, Inc.) the radio frequency voltage is controlled by a manual knob on the apparatus which is turned up by the neurosurgeon at the time of surgery. The temperature of the lesion electrode is monitored by thermometric readouts at the apparatus console. Temperature control is essential in these procedures for safety, effectiveness, and consistency of lesion size; this fact being established clearly over the last three decades. Several workers and commercially available apparatus use automatic temperature control, meaning that the apparatus cycles the RF voltage up automatically until the temperature control reaches a set temperature point, at which time the radio frequency power circuit is regulated to stabilize on that set temperature. This would be referred to as full automatic temperature control. Examples of apparatus that have automatic temperature control are illustrated by the Dutch Coagrader system in the 1960's and the Fischer lesion generator systems of the 1960's and most recently in the 1980's.

There are major problems with full automatic temperature control associated with safety and controllability. Radio frequency lesion electrodes vary in size dramatically from 0.25 mm in diameter all the way up to 3 mm in diameter or more. The amount of RF power required to heat these electrode tips to a given therapeutic temperature, such as 70 or 80 degrees (° C.), varies widely. Other variable factors involve tissue vascularity, impedance and various physiologic factors. A disastrous situation can take place if the RF power is increased so rapidly that the temperature swings very rapidly through a set temperature and feedback becomes unstable. The electrode tip surrounding temperature may rapidly exceed 100 degrees, the boiling point, gas will form, and one has a rapid decrease of lesioning current because of the higher impedance of the gas formation and a rapid degeneration of the temperature until the gas is absorbed. Then, with the RF level still high, boiling can reoccur, and one gets a violent oscillatory unstable heating situation. Production of gas and steam at the electrode tip can have catastrophic effects on surrounding tissue. Then the control, safety, and effectiveness of the automatic temperature control system is not reliable. One of the objectives of this patent is to describe a temperature control system, referred to as an over-temperature conrtrol, for such a heating system which both enables the operator to control a rise in temperature himself at the crucial time when instabilities could happen and yet provide stabilization at a final tip temperature which is desired. This hybrid control means has never been used before in therapeutic heating systems, whether they be radio frequency neurosurgical systems or other coagulation systems for other purposes in medicine.

DESCRIPTION OF THE INVENTION

FIG. 1 illustrates the basic schematic diagram showing one embodiment of this invention. Item 1 is an example of a radio frequency heating electrode that can be inserted into the body. It has a shaft which is insulated by insulation 2, except for an exposed tip 3, such that electrical contact made with the hub 4, which may also be conductive and connected to the shaft 1, will therefore activate the exposed tip at the potential of the hub, thereby driving radio frequency current through a medium of the body 5 to a reference or ground electrode 6 elsewhere on the body. If the ground electrode and the RF electrode are connected across an RF power source 7, then current will flow from exposed tip 3 to the reference electrode 6, thereby heating the tissue around exposed tip 3. A temperature sensor 8 in the tip of the electrode measures the tissue temperature in the vicinity of the tip 3 and thus the degree of heating. This is a standard arrangement for radio frequency (RF) heating within the body that is common in neurosurgery. Also common for such apparatus is a temperature measuring means 9 and also a readout means 10 where the operator can visualize the temperature at the electrode tip. In a typical lesion generator apparatus, for example, that offered by Radionics, Inc., which is the leading supplier of such equipment, the RF power source is controlled by a manual RF control knob, this being raised to increase the RF voltage across the tip 8 and electrode 6 so as to increase the current and therefore the heating. The operator looks at the temperature readout 10 and manually controls the RF power to the suited level. In other automatic lesion generator systems mentioned above, there is circuitry that provides an automatic increase in the RF power such that it will raise the electrode tip temperature; and when the temperature achieves a preset temperature point, the RF power from the power source is regulated, modulated, and otherwise controlled to stabilize around the set temperature. This would be the fully automatic control scheme and has been proposed for the last several decades by the above mentioned manufacturers.

The object of the present invention is the addition in the diagram of FIG. 1 of the automatic over-temperature control unit 11 which represents a hybrid between a fully automatic temperature control and a manual control unit. A manual set temperature means 12 is incorporated in the overtemperature control unit 11. Thus, a prescribed, desired end temperature can be set by the operator by 12. The RF power source 7 also has a manual level control knob or other means 13 which enables the operator to increase the RF power himself manually. In the operation of this system, a surgeon will start with a zero power level and increase the RF level by control 13. The temperature at the electrode tip 3 will increase as detected by temperature measuring unit 9. When the measured temperature of the sensor 8 thereby measured, achieves the set value of the over-temperature control unit 11, then there is means within 11 to moderate or modulate the output of RF power source 7 so as to tend to maintain the set temperature level of the over-temperature control unit 11 on the electrode tip 3. This is the general scheme of the present invention, namely the preservation of manual increase of the RF power level on the electrode, but adding an interposition of an automatic temperature control unit to moderate the RF power at the point where the temperature has reached the neighborhood of the set temperature so as to maintain the temperature at the electrode near the set temperature. Thus, it has the feature of stabilizing the tip temperature at the desired end point temperature, but still invokes the human control by the operator to raise the temperature during the critical phase of initial temperature rise and subsequent approach to the set temperature.

There is a multiplicity of ways and means to implement the automatic over-temperature control moderation of the RF power. Only a few will be cited here in this description, and it is obvious to those skilled in the art that many other implementations can be made. These are also intended to be included in the scope of the invention. For example, when the tip temperature of 3 becomes in the range of the set temperature, then the overtemperature control unit will turn the RF control source on and off to the electrode 1 at the correct duty cycle to maintain the desired tip temperature at the control level. This chopping of the RF power source will increase if the manual level 13 is also increased. If the manual level 13 is decreased below the critical level, then the chopping will cease. One can have, in addition, a means such that if the amount of off-to-on duty cycle or the percent of chopping becomes excessive, then the automatic over-temperature control can actually shut off the RF power source to prevent extremely high RF voltage levels that would be required to maintain only a given temperature, and thus to prevent the risk of sparking and burning during the on-portion of the cycle. Other means of automatic temperature control might by automatic takeover of the RF power voltage when the electrode temperature is near or has exceeded the set temperature, which would thus disable the manual control 13 at that point. These methods amount to a feedback-type interaction of the over-temperature control of the RF power source based on the temperature measuring means 19 information.

An obvious advantage of the present invention is that it maintains the human operator's interaction with the eqiupment in the critical phase of RF power increase to achieve a desired temperature. The reason this is important is manifold, but principally it is that a great variety of electrode sizes are used in such heating methods. In the spinal cord, for example, electrodes as small as ¼ mm in diameter may be used, whereas in the brain or elsewhere in the body, diameters of 2-4 mm are commonly used. Thus the degree of RF power source increase to achieve a given temperature varies widely. The time rate of change of this increase is critical since runaway to boiling could easily occur with severe injury to the patient. Thus, the manual and visual control by the surgeon is essential in raising the RF power level. Once the level has asymptoted to the region of the set temperature, however, it is therefore much easier for automatic temperature control circuitry to take over and maintain this level by the chopping or feedback method described above, or by other means familiar to those skilled in the art. Thus it is much safer to have this hybrid manual/automatic method than a fully automatic method where the instrumentation must somehow recognize the size of the electrode, the degree to which the rate of change of power increase should be applied for safety, and other variable factors such as tissue impedance, etc., which could moderate the physiologic and instrumentation interaction. It is obvious too that the over temperature control can be used to detect anomalies in the degree of RF power moderations to hold a given set temperature, such as transient spikes, which would indicate boiling, or excessive chopping of the RF power, which in turn would indicate a far-too-high setting of the manual control knob 13 on the power source. These ancillary features could be built into the over temperature control unit for further safety of the operation.

It is also clear that the exact block diagram indicated in FIG. 1 could be rearranged in a different topology or interconfiguration to achieve the same means. Again, those skilled in the art could interpret this diagram in a modified way with the same and effect.

It is further assumed in this patent that the radio frequency power source could be replaced by other forms of heat generation means. For example, microwave or low frequency heating electromagnetic sources could be used that could also be connected to electrodes. Simple DC electric sources could also be used in conjunction with resistant heating means that would affect the heating in the body. In this situation no ground or indifferent electrodes would be required since the probe itself would be heated (instead of the electromagnetic current heating of the tissue), the temperature of which is set by the temperature sensing measuring circuitry. One could even imagine ultrasonic, laser, or other forms of energy that can be transmitted from an energy source to an electrode which could be used to heat a tissue at the active end of a probe. The temperature sensors in the probe themselves can take varied forms; thermocouples, thermistors, thermosensor chips, integrated circuits, and other means. The appropriate temperature measuring circuitry or devices could be used to read out the temperature, and the monitoring of the temperature itself for the operator could be visualized on meters, digital displays, chart recordings, etc.

In practice, the manual output control 13 of the power source 7 might be raised so that the temperature measured by monitoring means 9 will increase and finally equal or slightly exceed the set-temperature set on manual unit 12 of the auto-temperature control 11. At this point the over-temperature control will regulate the power source unit so as to bring the measured temperature within some limits of the set-temperature set by unit 12. There would be some range about the set-temperature or some set-level such that the automatic over-temperature control would attempt to reduce or vary the RF power control or source such that its measured temperature will stay within set limits or depress the measured temperature below the set-temperature at all times. There might be time-averaging involved, electronic limit brackets in the over-temperature control active range, comparative limit levels to compare the measured to the set temperatures to control the over-temperature control regulation, etc. Other variants of this scheme can be thought of by people skilled in the art, but I claim this to be within the general scope of this patent.

The claims I wish to secure by Letters Patent in the U.S. Patent Office are the following:

1. An apparatus for combined manual and automatic over-temperature control of heating of biological bodily tissue by an electrode applied thereto, said apparatus comprising:

(a) Electromagnetic power source means having a manually actuated output level control means for manually raising or lowering the output power from said electromagnetic power source means applied to said electrode and thus raising and lowering the heating of said bodily tissue;

(b) Temperature measuring means adapted to be connected to said electrode, said electrode having a built-in temperature sensor such that said temperature measuring means detects the temperature sensed by said temperature sensor which in turn reflects the temperature of the tissue heated by said electrode;

(c) Over-temperature control means having means for manually setting a set-temperature, said over-temperature control means being cooperatively connected to said electromagnetic power source means and said temperature measuring means, whereby when the measured temperature, which can be raised by said manually actuated output level control means, approaches said set-temperature, the over-temperature control means will regulate the output of said electromagnetic power source means to maintain said measured temperature within a range relative to said set-temperature;

so that an operator can manually control the rise of said measured temperature in the critical phase when said bodily tissue is beginning to be heated by said electrode by raising said manually actuated output level control means, and can also achieve stabilization of said measured temperature near said set-temperature when said manually actuated output level control means reaches an output level where said measured temperature approaches said set-temperature.

2. The apparatus of claim 1 wherein said electromagnetic power source means is a radio-frequency power source generator, and wherein said manually actuated output level control means controls the radio-frequency voltage of said radio-frequency power source generator.

3. The apparatus of claim 1 wherein said over-temperature control means includes comparitor means to compare said measured temperature and said set-temperature, and includes regulation means, such that when said comparitor means detects that said measured temperature has exceeded said set-temperature by a predetermined amount, then said regulation means will reduce the output of said electromagneticpower source means so as to reduce said measured temperature below a predetermined temperature relative to said set-temperature.

4. The apparatus of claim 3 wherein said regulation means reduces said electromagnetic power source means output by turning said electromagnetic power source means output on and off from application to said electrode at a regulated rate, so as to reduce the heating of said bodily tissues and and thus to reduce said measured temperature.

5. The apparatus of claim 3 wherein said regulation means reduces said electromagnetic power source means output by overriding said manually actuated output control means when said measured temperature exceeds said set-temperature and reduces said electromagnetic power source means output to prevent said measured temperature from exceeding said set-temperature.

6. The apparatus of claim 4 further comprising duty-cycle detecting means cooperatively connected to said power source means such that if the duty-cycle of off versus on time of said electromagnetic power source means to said electrode exceeds a preset amount, then said electromagnetic power source means will be shut down by said duty-cycle detecting means.

* * * * *